United States Patent [19]

Aritomi et al.

[11] Patent Number: 4,653,078

[45] Date of Patent: Mar. 24, 1987

[54] METHOD AND APPARATUS FOR DETECTING OCCURRENCE OF CLOGGING CONDITIONS BY COUNTING PARTICLES SUSPENDED IN A LIQUID METHOD

[75] Inventors: Toshiaki Aritomi, Ibaraki; Hatsue Shinohara; Shinichi Sakuraba, both of Katsuta, all of Japan

[73] Assignee: Hitachi, Ltd., Tokyo, Japan

[21] Appl. No.: 721,468

[22] Filed: Apr. 9, 1985

[30] Foreign Application Priority Data

Apr. 9, 1984 [JP] Japan .................... 59-70455

[51] Int. Cl.⁴ .................... G01N 27/00
[52] U.S. Cl. .................... 377/10; 324/71.4
[58] Field of Search ............ 377/10, 12, 11; 324/71.1, 71.4

[56] References Cited

U.S. PATENT DOCUMENTS 3,259,842 7/1966 Coulter et al. .................... 377/12
3,768,084 10/1973 Haynes .................... 377/12
3,921,066 11/1975 Angel et al. .................... 377/12
3,973,194 8/1976 McMorris et al. .................... 324/71.1

Primary Examiner—John S. Heyman
Assistant Examiner—Karl Ohralik
Attorney, Agent, or Firm—Antonelli, Terry & Wands

[57] ABSTRACT

A method of counting red blood cells suspended in a blood sample is disclosed which can judge the presence or absence of clogging in the sample passage system of a blood cell counting apparatus. In this method, for example, the counting of red blood cells for a period of 200 msec is repeated 50 times, the means value $\overline{X}$ and standard deviation SD of 50 red blood cell counts each indicating the number of red blood cells per unit time (equal to 200 msec) are calculated, and when one of the red blood cell counts deviates from the mean value $\overline{X}$ by more than 3SD, such deviation is judged to presage clogging in the sample passage system. Further, each of the red blood cell counts can be displayed on the fluorescent screen of a CRT display.

11 Claims, 5 Drawing Figures

METHOD AND APPARATUS FOR DETECTING OCCURRENCE OF CLOGGING CONDITIONS BY COUNTING PARTICLES SUSPENDED IN A LIQUID METHOD

BACKGROUND OF THE INVENTION

The present invention relates to a method of counting particles suspended in a liquid medium, and more particulary to the above method suitable for use in an apparatus for counting blood cells in blood such as red blood cells and blood platelets so as to provide an indication of clogging conditions occurring in a liquid passage.

A method of automatically counting particles suspended in a liquid medium is used in a blood cell counter, and is classified into two typical methods, one of which utilizes changes in electric resistance due to particles, and the other uses scattered light from particles.

An example of a particle counting method based upon the detection of changes in electric resistance is disclosed in, for instance, U.S. Pat. No. 3,768,084. In this method, detector means having an aperture capable of passing a blood cell therethrough is used, and a pair of electrodes are disposed in the flow of a blood sample so that one electrode is on each side of the aperture, to cause an electric current to flow between the electrodes. When a blood cell passes through the aperture, the electric resistance between the electrodes varies pulsively. Not only the number of blood cells but also the size and volume of each blood cell can be known by measuring the state of resistance change.

A blood cell counting method based on the detection of scattered light is disclosed in, for example, a Japanese patent specification (Publication No. Sho. 51-24264 (1976)). In this method, a diluted blood sample passes through a flow cell in the state that the flow cell is irradiated with a thin light beam. When a blood cell passes through that portion of the flow cell which is irradiated with the thin light beam, light is scattered by the blood cell. Accordingly, the blood cell can be detected by measuring a change in the intensity of forward scattered light.

The above-mentioned two methods use a liquid passage system including the aperture or a small pipe serving as the flow cell, and therefore are encountered with a problem that the aperture or pipe may be clogged. Clogging readily takes place in the case where blood cells in a blood sample are agglutinated, and a great deal of labor is required to eliminate clogging.

Various measures have hitherto been taken to solve the clogging problem at the liquid passage system. For example, in the previously-referred U.S. Pat. No. 3,768,084, changes in electric resistance are detected to judge the presence or absence of aperture clogging. In more detail, when a large increase in resistance is detected continuously, it is judged that aperture clogging takes place, and an alarm is generated. However, such a method can detect aperture clogging only when an aperture is clogged to a remarkable extent, and can be used only in the particle counting method based upon the detection of changes in electric resistance.

SUMMARY OF THE INVENTION

An object of the present invention is to provide a method of counting particles suspended in a liquid medium, in which clogging in the liquid passage system of a particle counting apparatus can be predicted before the liquid passage system is completely clogged.

Another object of the present invention is to provide a method of finding clogging in a liquid passage system which is applicable not only to the particle counting method based upon the detection of changes in electric resistance but also to the particle counting method based upon the detection of scattered light.

In order to attain the above objects, a method of counting particles suspended in a liquid medium according to the present invention, comprising the steps of: causing a sample solution containing suspended particles to flow through detector means, to detect particles passing through the detector means; storing a particle count which indicates the number of particles detected by the detector means in a predetermined short time, in memory means; reading out a plurality of particle counts each indicating the number of particles detected in the predetermined short time, from the memory means, to calculate the mean value of the particle counts and a statistical error; judging that an abnormality is present in a liquid passage system, when one of the read-out particle counts lies outside a statistical error range; and displaying that an abnormality is present in the liquid passage system, on the basis of the above judgement.

In a preferred embodiment of the present invention, a flow cell included in a detector is irradiated with a laser beam, and light scattered by particles in a blood sample flowing through the flow cell is received by a photoelectric conversion element, to be converted into an electric signal. It is judged from red blood cell counts whether a tendency to clogging is present in a liquid passage system or not. In more detail, the counting of red blood cells for a short period is repeated 50 times for one blood sample. When the red blood cell counts thus obtained fluctuate widely, it is judged that a cause for clogging begins to generate in the liquid passage system. The sum of the red blood cell counts each obtained in the short period, is used for judging whether the blood sample is considered to be normal or not. Although a detector for detecting scattered light is used in the preferred embodiment, the present invention is also applicable to a particle counting method based upon the detection of changes in electric resistance.

DESCRIPTION OF THE PREFERRED EMBODIMENTS

Figure 1:
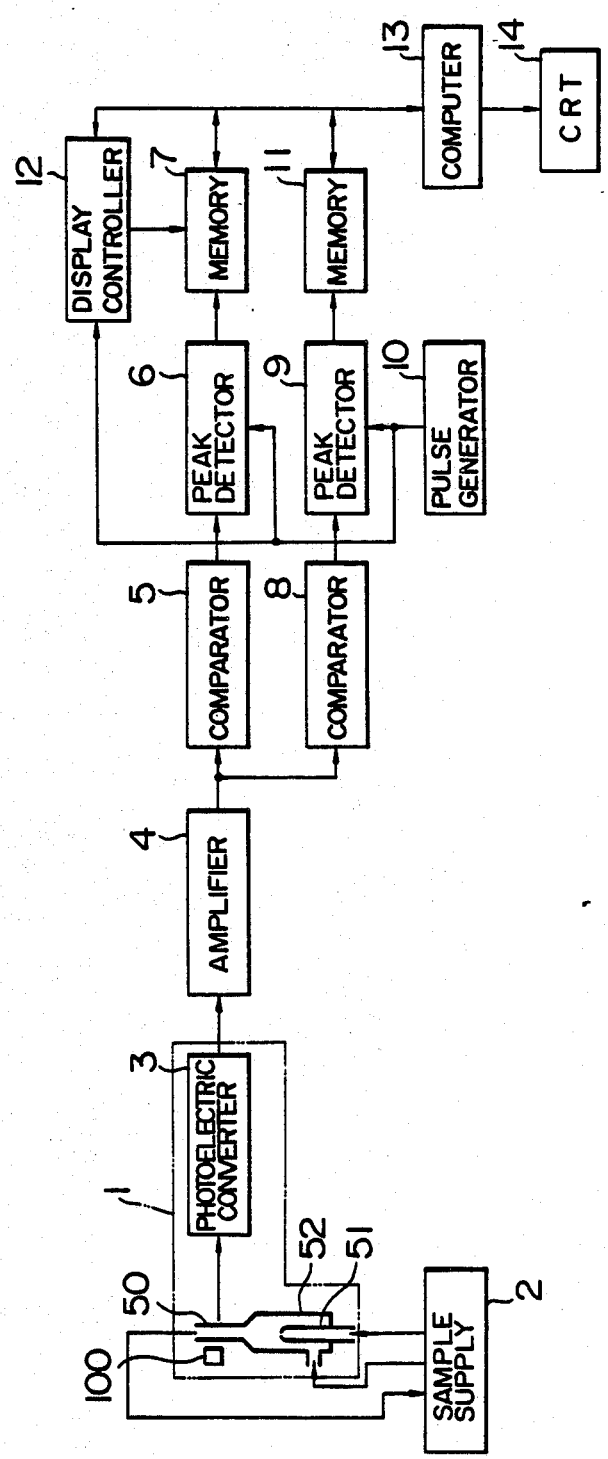
FIG. 1 is a schematic block diagram showing an embodiment of a particle counting apparatus according to the present invention.

FIG. 1 shows an embodiment of a particle counting apparatus according to the present invention, which is used as a blood cell counter. That is, the present embodiment is used for counting red blood cells and blood platelets suspended in a diluted blood sample.

Referring to FIG. 1, a detector 1 includes a flow cell 50, a light source 100, and a photoelectric conversion element 3. The flow cell 50 is connected with an outer tube 52 having an inner tube 51 therein. A diluted blood sample which is obtained by diluting one volume of blood with 500 volumes of diluent, is supplied from sample supply means 2 to the inner tube 51. An electrolytic solution is supplied, as a sheath liquid, from the supply means 2 to the outer tube 52. At this time, the diluted blood sample ejected from the inner tube 51 is surrounded with a sheath which is formed of the electrolytic solution supplied through an inlet for introducing the electrolytic solution into the outer tube 52, and thus forms a thin flow. The diameter of the flow of the diluted blood sample depends upon a ratio of the flow rate of the diluted blood sample to the flow rate of the electrolytic solution. When a particle flowing through the flow cell goes across the optical path of a laser beam emitted from the light source 100, light is scattered by the particle, and the scattered light is detected by the photoelectric conversion element 3. The conversion element 3 is connected to a comparator 5 for red blood cell and a comparator 8 for blood platelet, through an amplifier 4. In the comparator 5, the output signal of the amplifier 4 is compared with a reference value, so as to detect red blood cells. The comparator 5 is connected to a peak value measuring circuit 6, which converts the height of each peak included in the output signal of the comparator 5 (namely, each peak value of the output signal of the comparator 5) into a digital value in such a manner that clock pulses delivered from a clock pulse generator 10 are counted for a period corresponding to the peak height and the number of clock pulses in this period is used as the digital value. The digital value thus obtained is sent to a memory 7, which is formed so as to be able to store digital values corresponding to all peak portions in the output of the photoelectric conversion element 3. The memory 7 is connected to a computer 13 through a bus line, and the computer 13 is connected to a display device 14 such as a CRT display. The computer 13 is also connected to a display control 12 through the bus line, and the display controller 12 is connected to the memory 7. Further, the display controller 12 receives clock pulses from the clock pulse generator 10.

Meanwhile, the comparator 8 for blood platelet is connected to another peak value measuring circuit 9. In the comparator 8, the output signal of the amplifier 4 is compared with a reference value so as to detect blood platelets. The peak value measuring circuit 9 converts each peak value of the output signal of the compartor 8 into a digital value in such a manner that clock pulses delivered from the clock pulse generator 10 are counted for a period corresponding to the peak value and the number of clock pulses in this period is used as the digital value. The digital value thus obtained is sent to a memory 11, which has the same construction as the memory 7, and stores all digital values delivered from the peak value measuring circuit 9. The memory 11 is connected to the computer 13 and display controller 12 through the bus line.

Next, explanation will be made on the operation of the embodiment shown in FIG. 1.

A diluted blood sample to be inspected is supplied from the sample supply means 2 to the detector 3, to be introduced in the flow cell 50 in the form of a thin flow surrounded with a sheath which is formed of the electrolytic solution. In more detail, the diluted blood sample is injected into the outer tube 52 through a sample inlet at a predetermined flow rate, and then flows through the flow cell 50 stably in the form of laminar flow while being protected by a sheath formed of the electrolytic solution which is injected through the electrolyte inlet. The laser beam emitted from the light source 100 travels in a direction perpendicular to the axis of the flow cell 50, and reaches the flow cell 50 so as to be incident on the center of the thin flow of the diluted blood sample. Even when the laser beam impinges on the thin flow of the diluted blood sample, if no blood cell is present in this sample, scattered light will not be generated. On the other hand, when a blood cell suspended in the diluted blood sample is irradiated with the laser beam, scattered light is generated.

The scattered light thus generated is received by the photoelectric conversion element 3, and it is judged on the basis of the output of the conversion element 3 which of a red blood cell and a blood platelet is the cause for the scattered light. In more detail, forward scattered light which is generated by scattering the laser beam from the light source 100 by particles in the diluted blood sample, is converted by the photoelectric conversion element 3 into an electric signal, which is amplified by the amplifier 4. Thus, a pulse signal containing pulses different in pulse height, is sent from the amplifier 4 to the comparators 5 and 8.

In each of the comparators 5 and 8, the pulse signal from the amplifier 4 is compared with a reference value, which is equal to an intermediate value between the height (namely, the peak value) of a pulse obtained when a red blood cell passes through the flow cell 50, and the peak value of a pulse obtained when a blood platelet passes through the flow cell 50. In general, the peak value of the pulse due to the scattered light from a red blood cell is greater than the peak value of the pulse due to the scattered light from a blood platelet. In the case where it is judged by the comparator 5 that the peak value of a pulse included in the pulse signal from the amplifier 4 is greater than the reference value, the pulse is sent from the comparator 5 to the peak value measuring circuit 6. While, in the case where it is judged by the comparator 8 that the peak value of the above pulse is less than the reference value, the pulse is sent from the comparator 8 to the peak value measuring circuit 9. That is, a pulse which is delivered from the amplifier 4 in the case where a red blood cell in the diluted blood sample crosses the laser beam emitted from the light source 100, is applied to the peak value measuring circuit 6. A pulse which is delivered from the amplifier 4 in the case where a blood platelet in the diluted blood sample crosses the laser beam, is applied to the peak value measuring circuit 9. The peak value of the pulse from the comparator 5 is detected and held by the peak value measuring circuit 9. In this circuit 9, the peak value held as above is converted into a digital value in such a manner that clock pulses from the clock pulse generator 10 are counted by a counter during a period requisite for a capacitor which charges up in accordance with a time constant, to reach a voltage level equal to the peak value, and the number of clock pulses supplied to the counter in the above period is used as the digital value. The digital value thus determined is sent to the memory 11.

The digital value from the peak value measuring circuit 6 is used as an address in the memory 7 which is formed of, for example, a semiconductor memory. In more detail, pulses having the peak value corresponding to the digital value are successively accumulated and counted, and the number of pulses having the above peak value is written in the memory 7 at the above address. That is, in the case where three pulses each corresponding to a red blood cell and having a peak value $V_1$ are delivered from the comparator 5, a digital value $D_{V1}$ corresponding to the peak value $V_1$ is used as an address, and a number 3 is stored in the memory 7 at the above address. Similarly, in the case where ten pulses corresponding to red blood cells and having a peak value $V_2$ are delivered from the comparator 5, a digital value $D_{V2}$ corresponding to the peak value $V_2$ is used as an address, and a number 10 is stored in the memory 7 at this address.

The contents of the memory 7 are read out by the display controller 12 at intervals of a predetermined time (for example, 200 msec), on the basis of clock pulses from the clock pulse generator 10, and red blood cells are counted up by the computer 13 to display red blood cell counts each indicating the number of red blood cells detected in the predetermined time, on the display device 14.

The total time required for performing a favorable counting operation for one diluted blood sample is 10 sec. This total time is the sum of equal time intervals. In other words, the total time is divided into 50 equal time intervals, and therefore each time interval is equal to 200 msec. The above time interval and the number of equal time intervals can be changed in accordance with a particle counting apparatus. The number of red blood cells detected in each time interval, that is, in a period of 200 msec, is displayed on the fluorescent screen of the CRT included in the display device 14. Further, the total number of red blood cells and the volume distribution of red blood cell can be displayed in the course of measurement for one diluted blood sample or after the measurement for one diluted blood sample has been completed. The above display can be carried out by reading out the contents of the memory 7 by the display controller 12 under control of the computer 13.

The peak value of the pulse from the comparator 8 is detected and held by the peak value measuring circuit 9. In this circuit 9, the peak value held as above is converted into a digital value in the same manner as in the peak value measuring circuit 6, that is, in such a manner that clock pulses from the clock pulse generator 10 are counted by a counter during a period requisite for a capacitor which charges up in accordance with a time constant, to reach a voltage level equal to the peak value, and the number of clock pulses supplied to the counter in the above period is used as the digital value. The digital value thus obtained is sent to the memory 11. Unlike the memory 7, the memory 11 may not be controlled by the display controller 12. This is because an abnormality in the liquid passage system can be detected from information on red blood cells and thus it is not required to use measured data on blood platelets for the purpose of judging the presence or absence of an abnormality in the liquid passage system. However, in order to obtain the total number of pulses corresponding to blood platelets and having the same peak value, for many peak values, the memory 11 may be connected to the display controller 12. Needless to say, measured data on blood platelets may be used for judging the presence or absence of an abnormality in the liquid passage system.

In addition to the result of measurement on red blood cells and blood platelets, the presence of an abnormality in the liquid passage system of the present embodiment can be displayed on the display device 14. The presence or absence of an abnormality in the liquid passage system is judged on the basis of whether variation in the number of red blood cells detected in a predetermined short period lie in a statistical error range, as will be explained later.

Figure 2:
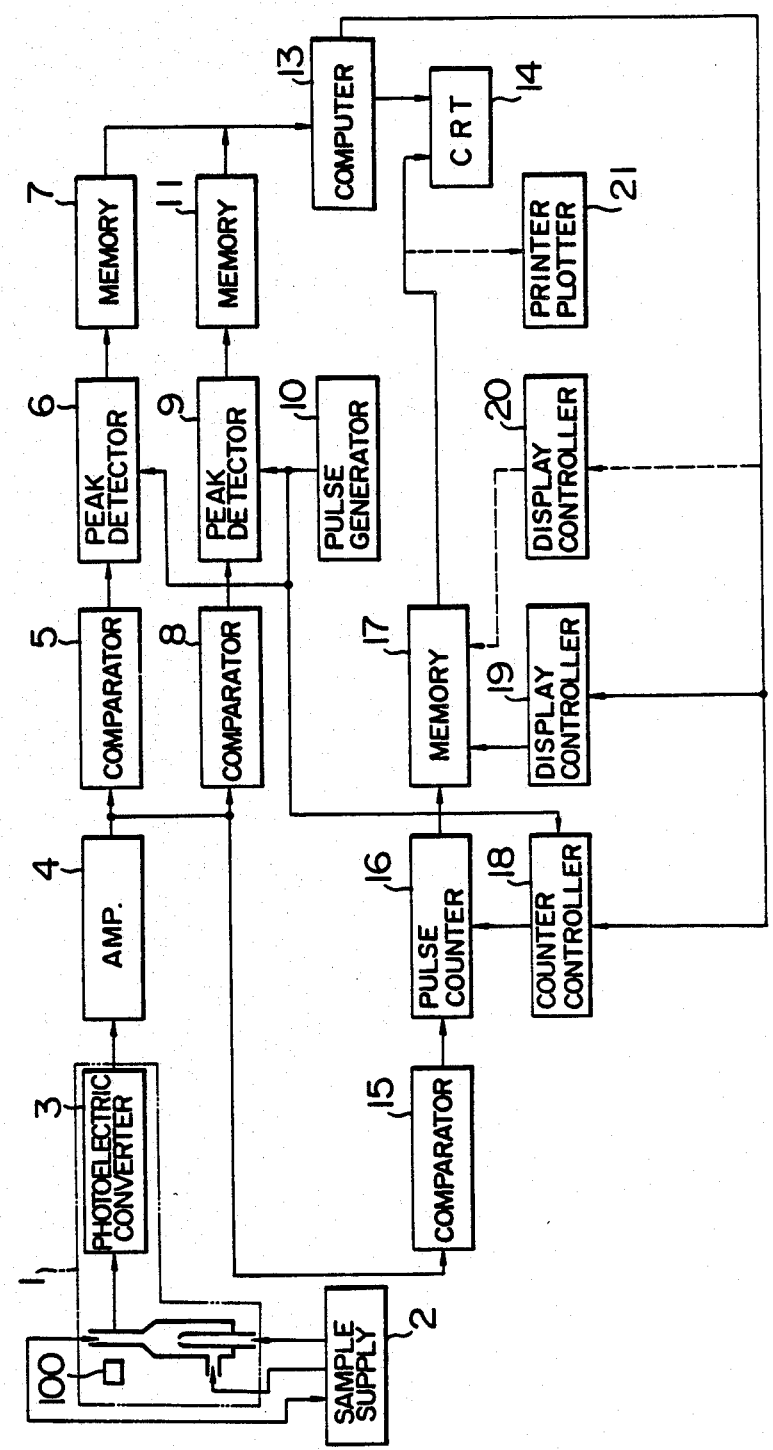
FIG. 2 is a schematic block diagram showing another embodiment of a particle counting apparatus according to the present invention.

FIG. 2 shows another embodiment of a particle counting apparatus according to the present invention. In FIG. 2, the same reference numerals as in FIG. 1 designate identical or equivalent parts.

The embodiment of FIG. 2 is different from the embodiment of FIG. 1 in that a circuit is additionally provided for counting pulses from the amplifier 4 without subjecting the pulses to analog-digital conversion. That is, the amplifier 4 is also connected to a comparator 15, which is connected to a pulse counter 16. The counter 16 is connected to a memory 17, which is connected to the display device 14. Further, a counter controller 18 is connected to the pulse counter 16, to control the counter 16 on the basis of a signal from the computer 13. Furthermore, the contents of the memory 17 can be displayed in the form of a graph on a display device 21 including a printer and a plotter, on the basis of a control signal from a display controller 20.

Figure 3:
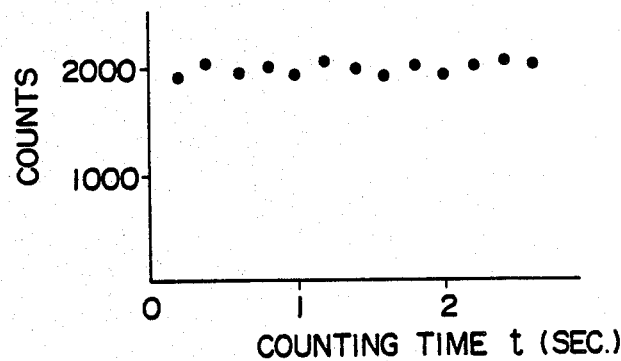
FIGS. 3 and 4 are graphs showing examples of measured data.
Figure 4:
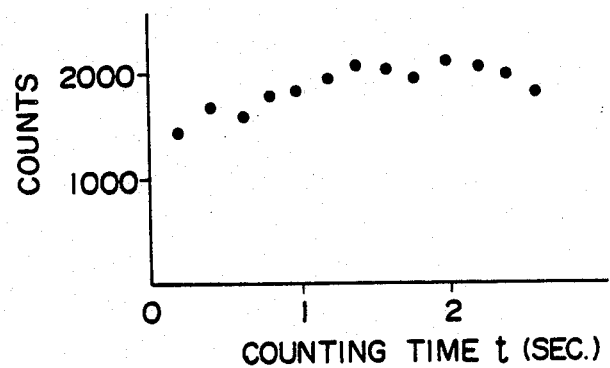

Referring to FIG. 2, respective peak values of pulses from the amplifier 4 are compared, by the comparator 15, with the same reference value as in the comparator 5. Pulses having peak values greater than the reference value, that is, pulses corresponding to red blood cells are counted by the pulse counter 16. A counting period, during which the pulses from the comparator 15 are continuously counted by the pulse counter 16, is controlled in such a manner that clock pulses from the clock pulse generator 10 are counted by the counter controller 18 on the basis of a control command from the computer 13 and a gate for the pulse counter 16 is closed when the number of clock pulses reaches a predetermined number. The output of the pulse counter 16 is stored in the memory 17 at intervals of a unit time equal to the above-mentioned counting period. The counts each obtained in the unit time are successively displayed on the display device 14 on the basis of a control signal which is supplied from the computer 13 through the display controller 19. When the contents of the memory 17 are displayed on the display device 21 under control of the display controller 20 (which is controlled by a signal from the computer 13), the counts each obtained in the unit time are displayed in the form of a graph, as shown in FIGS. 3 and 4, and thus the stability of the liquid passage system can be known at a glance. For instance, in the case where the count per unit time fluctuates widely and increases or decreases for a considerable time, as shown in FIG. 4, it is judged that an abnormality is present in the liquid passage system.

As mentioned above, according to the embodiment of FIG. 2, the pulses delivered from the comparator 15 are counted by the pulse counter 16, without being converted into a digital value, and therefore a pulse counting time can be shortened.

Figure 5:
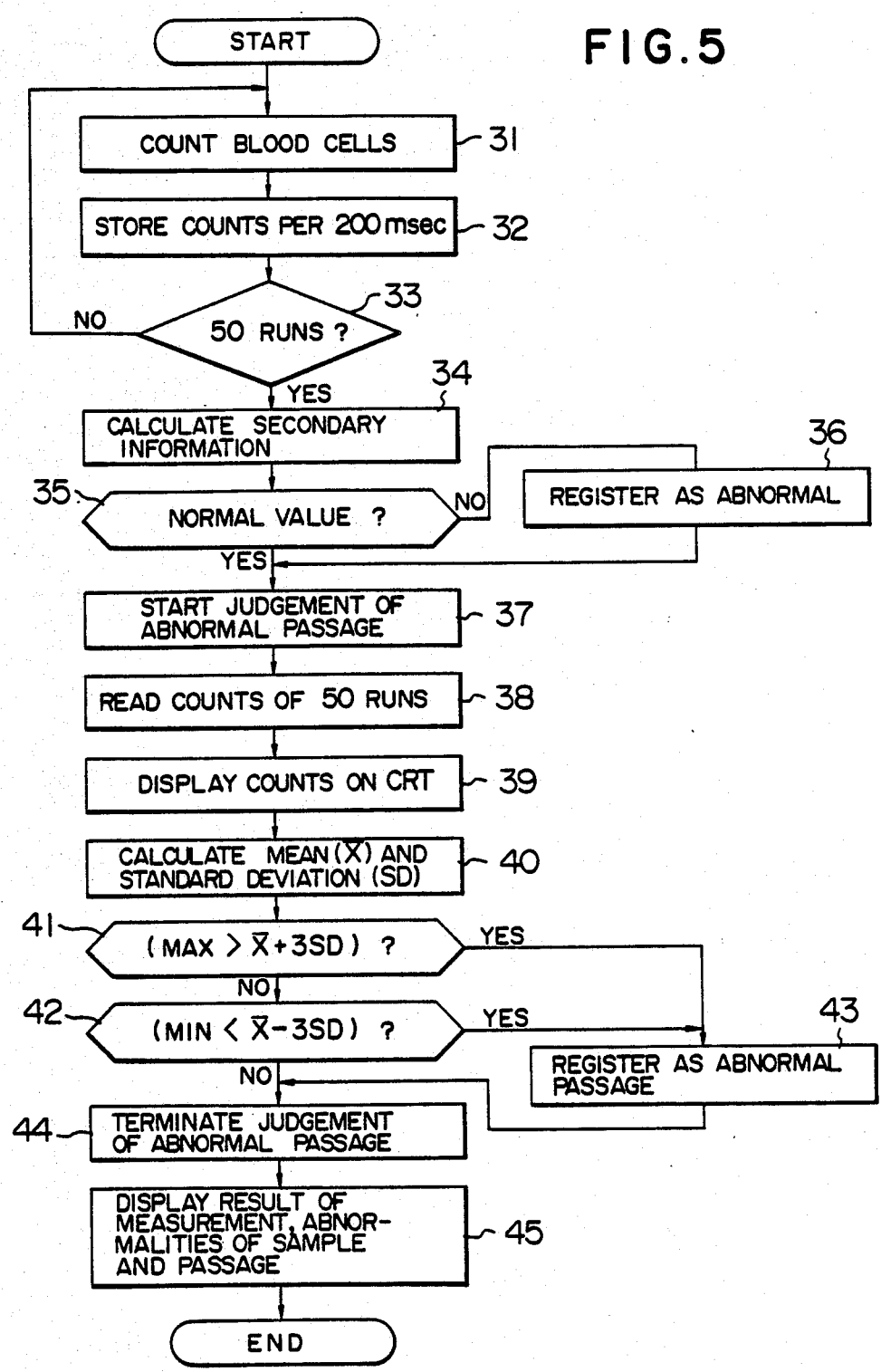
FIG. 5 is a flowchart showing the opeation of the embodiment of FIG. 2.

FIG. 5 shows a flowchart for explaining a measuring operation which uses the embodiment of FIG. 2.

A plurality of blood samples are set in the sample supply means 2. When measurement is started, the blood samples are sucked by a sampling nozzle at intervals of a predetermined time (for example, 30 sec.), and a blood sample is diluted by mixing one volume of blood sample with e.g. 500 volumes of diluent. The diluted blood sample thus obtained is introduced into the flow cell 50 at a predetermined flow rate. Then, a blood cell counting operation is started (step 31 of FIG. 5). At the blood cell counting operation, the number of white blood cells contained in 1 μg of blood, the number of red blood cells contained in 1 μg of blood, the number of blood platelets contained in 1 μg of blood, the amount of hemoglobin contained in red blood cell, and a hematocrit value are determined.

Each time a particle passes through the flow cell 50, the number of particles which are equal in kind to the particle and have passed through the flow cell 50, are stored in some memories. In FIG. 5, however, only the counting of red blood cell is explained. In step 32, the number of red blood cells detected in a period of 200 msec is readably stored in the memory 17 at intervals of 200 msec. The counting of red blood cells for a period of 200 msec is repeated 50 times, that is, 50 measured data are obtained in a period of 10 sec. (step 33). In step 34, calculation for obtaining the average volume of red blood cell, the average of the amount of pigment contained in one red blood cell, and the average of the pigment concentration in red blood cell, are carried out on the basis of blood cell information obtained in step 31. Then, it is judged in step 35 whether the information obtained in step 34 lies in a range corresponding to normal blood or not. This range is previously inputted to judgment means by a doctor or examining expert. When the information lies outside the range, it is registered that the blood sample is abnormal (step 36), and then the processing in step 37 is carried out. When the above information lies in the range, the processing in step 37 is immediately carried out. In step 37, an operation for judging the presence or absence of an abnormality in the liquid passage system is started. In step 38, 50 counts each indicating the number of red blood cells per unit time (equal to 200 msec) are read out from the memory 17. The read-out counts are immediately displayed on the display device 14. Part of displayed data is shown in FIG. 3. Referring to FIG. 3, the above counts are displayed at intervals of 200 msec. Incidentally, FIG. 3 shows the case where no clogging is present in the liquid passage system. While, FIG. 4 shows the case where a tendency to clogging is present in the liquid passage system.

In step 40, the mean value $\overline{X}$ of the counts each indicating the number of red blood cells per unit time and the standard deviation SD of the counts are calculated on the basis of data which is read out from the memory 17 in step 38, and a statistical error range is determined to be used as an allowable range. In the present measuring operation, for example, upper and lower limits of the statistical error range are given by $(\overline{X}+3SD)$ and $(\overline{X}-3SD)$, respectively. It is judged in step 41 whether the largest one of the counts is greater than the upper limit $(\overline{X}+3SD)$ or not. When the largest count is greater than the upper limit, an abnormality in the liquid passage system is registered (step 43). Further, it is judged in step 42 whether the smallest of the counts is less than the lower limit $(\overline{X}-3SD)$ or not. When the smallest count is less than the lower limit, an abnormality in the liquid passage system is registered (step 43). In other words, when the largest or smallest count lies outside the range $(\overline{X}\pm3SD)$ corresponding to the normal state of the liquid passage system, it is stored in the memory 17 that an abnormality is present in the liquid passage system. Thus, the operation for judging the presence or absence of abnormality in the liquid passage system is completed (step 44).

When it is judged in steps 41 and 42 that all the counts lie in the range corresponding to the normal state of the liquid passage system, only the result of measurement is displayed on the display device 21 (step 45). In the case where it is registered in step 36 that the blood sample is abnormal, a mark for indicating an abnormal blood sample is appended to the result of measurement on red blood cells when this result is printed out (step 45). Further, in the case where an abnormality in the liquid passage system is registered in step 43, a message indicating the contents of the registration is printed out by the display device 21, together with the result of measurement. Thus, an operator can clear the liquid passage system before clogging therein becomes serious.

The judgement in steps 41 and 42 is made on the basis of the following facts. The counts each indicating the number of red blood cells detected in a predetermined time, are considered to be normally distributed. Accordingly, in the case where the liquid passage system is kept at a normal state and variations in the count which indicates the nubmer of red blood cells detected in the predetermined time, are caused only by a statistical error, 99.7% of the counts will indicate a value within a range whose upper and lower limits are given by $(\overline{X}+3SD)$ and $(\overline{X}-3SD)$, respectively. Thus, in the case where the largest, the smallest or a given one of the counts lies outside the above range, it is considered that an abnormality is present in the liquid passage system, and necessary processing is carried out. That is, the counts each indicating the number of red blood cells per unit time (equal to the predetermined time) are required to satisfy the following formulae:

$$(\text{maximum count} - \text{means value } \overline{X}) \leq 3SD$$

$$(\text{mean value } \overline{X} - \text{minimum count}) \leq 3SD.$$

Accordingly, in the case where one of the counts is greatly deviated from the range whose upper and lower limits are given by $(\overline{X}+3SD)$ and $(\overline{X}-3SD)$, respectively, or several counts other than the largest and smallest counts lie outside the above range, it can be judged that an abnormality is present in the liquid passage system.

We claim:

1. A method of detecting clogging conditions occurring in a liquid passage system by counting particles suspended in a liquid medium, comprising the steps of:
   causing a sample solution containing suspended particles to flow through detector means to detect particles passing through said detector means;
   repeatedly counting the number of particles detected by said detector means in each of predetermined short time periods jointly constituting a total count period for one sample, and storing the respective counts in memory means;
   reading out the particle counts for respective short time periods, from said memory means, and calculating an allowable range for the particle counts based upon the read-out counts;
   detecting that a condition of clogging occurrence is present in the liquid passage system, when variation of the counts for the same sample exceeds the allowable range; and
   displaying the clogging condition detection result;

2. A method according to claim 1, wherein each of said particle counts indicates the number of red blood cells in blood.

3. A method according to claim 1, further comprising, after the particle count storing step, a step of reading out a particle count which indicates the number of particles detected in a respective predetermined short time period, from said memory means to display the read-out particle count on a display device.

4. A method according to claim 1, wherein said detector means is constructed so as to utilize changes in electric resistance due to particles.

5. A method of counting particles suspended in a liquid medium according to claim 1, wherein a total time which is the sum of successive time intervals each equal to said predetermined short time, is required for completing a particle counting operation for one sample solution, and it is judged on the basis of the number of particles detected in said total time whether said sample solution is to be considered to be normal or not.

6. A method of detecting clogging conditions occurring in a liquid passage system by counting particles suspended in a liquid medium, comprising the steps of:
causing the diluted blood sample to flow through a flow cell;
irradiating said flow cell with light to detect scattered light from a red blood cell, and to convert said scattered light into an electric signal;
detecting a red blood cell by comparing said electric signal with a reference;
storing the number of red blood cells passing through said flow cell in a predetermined short time;
repeating the counting of red blood cells passing through said flow cell in said predetermined short time, for said diluted blood sample a plurality of times;
judging whether said diluted blood sample is to be considered to be normal or not, on the basis of the number of red blood cells detected in a total time required for said repetition;
calculating the mean value of plurality of stored red blood cell counts each indicating the number of red blood cells detected in said predetermined short time, and a statistical error range with respect to said red blood cell counts;
detecting that there is no danger of clogging taking place in the liquid passage system, when at least one of said red blood cell counts lie outside of the statistical error range; and
displaying said red blood cell counts each indicating the number of red blood cells detected in said predetermined short time, on a display device.

7. An automated, fail-safe particle counting system and clogging condition detector comprising;
means for repeatedly counting particles in a predetermined quantity of a sample specimen of same origin;
means for storing the respective counts in a memory;
means for reading out the stored counts and calculating an average count and a predetermined statistical error range, and setting an allowable range; and
means for comparing each count with the allowable range and for detecting when a count is outside the allowable range as an indication of a clogging condition occurring in a sample passage system of the particle counting system.

8. A method according to claim 1, wherein the calculating of an allowable range for the particle counts based upon the read-out counts includes calculating the mean value of the read-out counts and a statistical error range therefor, and the detection of clogging condition occurrence is detected when one of the read-out counts lies outside the statistical error range.

9. A method according to claim 1, further comprising the step of displaying a count of particles per unit volume for the detected sample.

10. A method according to claim 1, wherein said detector means is constructed so as to utilize scattered light from particles.

11. An automated, fail-safe particle counting system and clogging condition detector according to claim 7, further comprising means for generating an alarm in response to detection of a clogging condition occurring in the sample passage system.

* * * * *